United States Patent [19]

Van Der Aalst et al.

[11] Patent Number: 5,600,045

[45] Date of Patent: Feb. 4, 1997

[54] PROCESS FOR CONVERSION OF CRUDE HYDROCARBON MIXTURES

[75] Inventors: Matheus J. Van Der Aalst, EC Terneuzen, Netherlands; Levien J. Everaert, Stekene, Belgium; Juan M. Garces, Midland, Mich.

[73] Assignee: The Dow Chemical Company, Midland, Mich.

[21] Appl. No.: 160,634

[22] Filed: Dec. 2, 1993

[51] Int. Cl.$^6$ .......... C07C 41/08; C07C 43/00; C07C 5/08; C07C 7/167

[52] U.S. Cl. .......... 585/261; 585/259; 568/688; 568/689; 568/697

[58] Field of Search .......... 585/3, 264, 270, 585/276, 259, 261; 44/449; 568/697, 688, 689

[56] References Cited

U.S. PATENT DOCUMENTS

| | | | |
|---|---|---|---|
| 4,605,787 | 8/1986 | Chu et al. | 568/697 |
| 4,891,448 | 1/1990 | Garces et al. | 568/628 |
| 4,950,820 | 8/1990 | Schleppinghoff et al. | 585/264 |
| 4,962,239 | 10/1990 | Bell et al. | 568/697 |
| 5,084,070 | 1/1992 | Kohler et al. | 44/449 |
| 5,489,719 | 2/1996 | Le et al. | 585/261 |

FOREIGN PATENT DOCUMENTS

| | | |
|---|---|---|
| 0055045 | 12/1981 | European Pat. Off. . |
| 0573185 | 12/1993 | European Pat. Off. . |
| 0133661 | 1/1979 | Germany . |
| 3813689 | 4/1988 | Germany . |

OTHER PUBLICATIONS

*Ind. Eng. Chem. Res.*, Preparation of Methyl tert–Buryl Ether (MTBE) Over Zeolite Catalyst, Pochen Chu and Gunter H. Kuhl, 1987, 26, pp. 365–369.

*Chem. Eng. Comm.*, Synthesis of Methyl Tertiary–Butyl Ether on HZSM–5 Zeolite, S. I. Pien and W. J. Hatcher, 1990, 93, pp. 257–265.

*Chemical Engineering*, Multi–Ether Processes Boost Gasoline Octane, Herb Short, Jun. 23, 1986 pp. 34–35.

Erdöl and Kohle–Erdgas, Petrochemie vereinigt mit brennstoff–Chemie, Novel Catalyst Widens Octane Opportunities, G. Pritchard and B. Schleppinghoff, Bd. 41, Heft 4, Apr., 1988, pp. 157–160.

*Primary Examiner*—Asok Pal
*Assistant Examiner*—Bekir L. Yildirim

[57] ABSTRACT

A process for conversion of crude hydrocarbon mixtures comprising tertiary olefins and gum-forming constituents with an alcohol in the presence of hydrogen, which process comprises contacting the crude hydrocarbon mixture, the alcohol, and hydrogen with a catalyst comprising an acidic molecular sieve containing an active hydrogenation metal component, as well as a stabilized crude hydrocarbon mixture containing alkyl tertiary alkyl ethers. A process for conversion of a tertiary olefin which contains one or more additional ethylenically or acetylenically unsaturated bonds.

22 Claims, No Drawings

PROCESS FOR CONVERSION OF CRUDE HYDROCARBON MIXTURES

Background of the Invention

The present invention relates to a process for conversion of crude hydrocarbon mixtures comprising tertiary olefins and gum-forming constituents and to the thus stabilized crude hydrocarbon mixture. This invention also relates to a process for conversion of a tertiary olefin which contains one or more additional ethylenically or acetylenically unsaturated bonds.

Ether compounds and especially alkyl tertiary alkyl ethers are valuable additives for gasoline blends. Exemplary of such alkyl tertiary alkyl ethers are methyl-tertiary butyl ether (MTBE), ethyl-tertiary butyl ether (ETBE) and methyl-tertiary amyl ether (TAME). These ether compounds are usually prepared by catalytic etherification of tertiary olefins with an alcohol, for example, etherification of isobutylene with methanol (to MTBE), etherification of isobutylene with ethanol (to ETBE) and etherification of 2-methyl-2-butene or 2-methyl-1-butene with methanol (to TAME). The tertiary olefin starting compounds are generally not used in substantially pure form, but in admixture with various other saturated and unsaturated hydrocarbon compounds having about the same number of carbon atoms. Such mixtures are also referred to as crude hydrocarbon mixtures which may be obtained as coproducts in steam cracking or catalytic cracking of hydrocarbon feedstock or other hydrocarbon conversion processes. Typical crude hydrocarbon mixtures are crude $C_4$, crude $C_5$, crude $C_{5-9}$ and crude $C_{6-10}$ mixtures, which are available in large quantities in the petrochemical and refining industries.

It is known to etherify such crude hydrocarbon mixtures to provide etherified crude hydrocarbon mixtures which contain alkyl tertiary alkyl ether compounds, such as for example MTBE, ETBE and TAME.

Under etherification conditions, gum-forming constituents, for example reactive multiple ethylenically or acetylenically unsaturated hydrocarbons, such as linear and branched diolefins and acetylenic compounds, present in crude hydrocarbon feedstock undergo oligomerization reactions leading to the formation of gums. The gums formed in the liquid phase or on the catalyst tend to adhere to or clog the catalyst and so cause a decrease in activity thereof eventually leading to complete deactivation. On the other hand, when the etherified crude hydrocarbon mixtures are used as or blended into gasoline or fuel, the gums contained therein lead to coke formation and deposits in the combustion chamber of an engine. Further, in case the etherified crude hydrocarbon mixture still contains gum-forming constituents, the etherified crude hydrocarbon mixture is not storage stable as these constituents give additional gum formation during storage and use.

In order to prevent gum formation, either during the etherification process or while stored or used, it has been proposed to first selectively hydrogenate the gum-forming constituents to remove excess unsaturation prior to the etherification reaction.

DE-A-3,813,689 discloses a process for the conversion of branched olefins with alkanols in the presence of hydrogen, by using catalytically active clays containing a hydrogenation active metal. The crude hydrocarbon mixture used in the examples of DE-3,813,689 contains only a minor percentage of a diolefin, i.e., 2.7 weight percent of isoprene. A disadvantage of this process is that the clay catalyst has a tendency to collapse at the elevated temperatures required for regenerating the catalyst. Reuse of the clay catalyst therefore is unsatisfactory.

U. S. Pat. No. 5,084,070 discloses a process to prepare a gum-free fuel containing alkyl tertiary alkyl ethers by etherification and hydrogenation of a crude hydrocarbon mixture containing straight chain and/or branched and/or cyclic saturated and mono-unsaturated hydrocarbons with 5 to 8 carbon atoms and furthermore containing gum-forming constituents and containing one or more tertiary olefins with an alcohol and hydrogen over a macroporous or gelatinous cation exchanger in the $H^+$ or acidic form, the cation exchanger comprising a hydrogenation metal component selected from the groups 6–10 of the Periodic Table of the Elements in the elemental form. The amount of gum-forming constituents allowed in the crude hydrocarbon mixture should not exceed 5 weight percent. A disadvantage of this process is that the cation exchange resins used in the process degrade at the elevated temperatures at which the hydrogenation metal compounds to be applied onto the cation exchange resin by usual methods in the art, such as by impregnation, are decomposed to the elemental form. Accordingly, other measures are required to load the hydrogenation metal onto the cation exchange resin which lead to an expensive catalyst. A further disadvantage of this process is that the hydrogenation metal loaded cation exchange catalyst, due to its thermal instability cannot be regenerated by the usual heat treatment at elevated temperatures so that other more cumbersome and expensive regeneration methods are required.

It is an object of the present invention to provide a stable process for preparing alkyl tertiary alkyl ethers from crude hydrocarbon mixtures comprising tertiary olefins and gum-forming constituents.

It is a further object of the invention to provide a process for preparing alkyl tertiary alkyl ethers from crude hydrocarbon mixtures comprising tertiary olefins and gum-forming constituents to form a stabilized hydrocarbon mixture with a substantially reduced gum content and with a substantially reduced gum-forming ability.

It is another object of the present invention to provide a stabilized hydrocarbon mixture containing alkyl tertiary alkyl ethers for gasoline or fuel blending purposes.

It is yet another object of the present invention to provide a process for preparing alkyl tertiary alkyl ethers from crude hydrocarbon mixtures comprising tertiary olefins and gum-forming constituents in the presence of an easily regenerable catalyst.

It is furthermore an object of the present invention, in a preferred embodiment, to provide a stable process for preparing alkyl tertiary alkyl ethers from crude hydrocarbon mixtures comprising tertiary olefins and high amounts of gum-forming constituents.

It is yet a further object of the present invention, in a preferred embodiment, to provide a process for preparing alkyl tertiary alkyl ethers from crude hydrocarbon mixtures comprising tertiary olefins and high amounts of gum-forming components, to form a stabilized hydrocarbon mixture with a substantially reduced gum content, a substantially reduced gum-forming ability, and an increased amount of alkyl tertiary alkyl ethers also due to conversion of undesired gum-forming constituents to valuable alkyl tertiary alkyl ethers.

It is still another object of the present invention, in a preferred embodiment, to provide a stabilized hydrocarbon mixture with a substantially reduced gum content, a substantially reduced gum-forming ability, and an increased amount of alkyl tertiary alkyl ethers due to conversion of undesired gum-forming constituents, having added value for gasoline or fuel blending purposes.

It is furthermore an object of the present invention to provide a process for conversion of a tertiary olefin which contains one or more additional ethylenically or acetylenically unsaturated bonds.

SUMMARY OF THE INVENTION

The present inventors have found that a specific type of catalyst is able to convert by simultaneous etherification and hydrogenation crude hydrocarbon mixtures comprising tertiary olefins and gum-forming constituents, without substantial deactivation over a prolonged period of time, giving etherified crude hydrocarbon mixtures with very low gum content and very low residual gum-forming constituents content, which catalyst is easily regenerable.

In a preferred embodiment of the present invention, the inventors surprisingly found that specific gum-forming constituents, i.e., a tertiary olefin which contains one or more additional ethylenically or acetylenically unsaturated bonds such as isoprene, can be converted to valuable alkyl tertiary alkyl ethers, even when present in high amounts.

Accordingly, the present invention provides a process for conversion of crude hydrocarbon mixtures comprising tertiary olefins and gum-forming constituents with alcohols in the presence of hydrogen, which process comprises contacting the crude hydrocarbon mixture, the alcohol, and hydrogen with a catalyst comprising an acidic molecular sieve containing an active hydrogenation metal component.

In another aspect, the present invention provides a stabilized crude hydrocarbon mixture containing alkyl tertiary alkyl ethers obtained by contacting a crude hydrocarbon mixture comprising tertiary olefins and gum-forming constituents, an alcohol, and hydrogen with a catalyst comprising an acidic molecular sieve containing an active hydrogenation metal component.

In a further aspect the present invention provides a process for conversion of a tertiary olefin which contains one or more additional ethylenically or acetylenically unsaturated bonds, which process comprises contacting the hydrocarbon compound, an alcohol, and hydrogen with a catalyst comprising an acidic molecular sieve containing an active hydrogenation metal component.

DETAILED DESCRIPTION OF THE INVENTION

All reference to the Periodic Table of the Elements herein shall refer to the Periodic Table of the Elements, published and copyrighted by CRC Press, Inc., 1989.

The crude hydrocarbon mixture to be employed in the process of the present invention contains tertiary olefins, suitable examples of which are tertiary mono-olefins containing 4 to 10 carbon atoms, such as isobutene, isopentene, isohexene and other branched mono-olefins.

The gum-forming constituents present in the crude hydrocarbon mixtures are typically unsaturated compounds polymerizable or oligomerizable under etherification conditions, such as linear and branched diolefins and acetylenic compounds.

The crude hydrocarbon mixture may further comprise other saturated or mono- or multiple unsaturated hydrocarbon compounds.

Crude hydrocarbon mixtures with various carbon atom numbers and varying degrees of unsaturation are available in petrochemical, refining and hydrocarbon conversion industries. These crude hydrocarbon mixtures can be obtained, for example, in the reaction of naphtha, liquid petroleum gas, crude oil distillates, gas oil or other hydrocarbon mixtures in steam crackers, catalytic crackers, isomerization or dehydrogenation plants. They can be employed in the present process as such with a relatively wide range of carbon atom numbers such as $C_{5-9}$- or $C_{5-10}$-mixtures, or narrower cuts which essentially contain, for example, $C_4$-, $C_5$- or $C_6$-hydrocarbons. Typically, a standard hydrogenation treatment of crude hydrocarbons takes place in a petrochemical or refining industry upon recovery of the crude hydrocarbon mixture, thus reducing the amount of gum-forming constituents. According to the present invention a crude hydrocarbon mixture does not need to be subjected to a separate hydrogenation step, or in other words, can by-pass such step as the present process is capable of etherifying and hydrogenating such mixtures even with high amounts of gum-forming constituents in one and the same step.

The catalysts to be employed in the present process are capable of converting tertiary olefins contained in crude hydrocarbon mixtures which also contain relatively high contents of gum-forming constituents. Preferably, the crude hydrocarbon mixture contains more than 5 weight percent, advantageously from about 6 to about 70 weight percent, and more preferably from about 10 to about 60 weight percent of gum-forming constituents. Even at such high concentrations of gum-forming constituents the catalysts maintain their activity for a prolonged period of time.

Preferably, the tertiary olefin in the crude hydrocarbon mixture comprises at least one tertiary olefin selected from the group consisting of isobutylene, 2-methyl-1-butene, 2-methyl-2-butene, 2-methyl-1-pentene, and 2-methyl-2-pentene.

Preferably the gum-forming constituent comprises a tertiary olefin which contains one or more additional ethylenically or acetylenically unsaturated bonds. It has been found by the inventors that this type of branched multiple unsaturated compound, the presence of which would be undesirable from the point of view that it is a gum-forming constituent, can be converted by the present process to valuable alkyl tertiary alkyl ethers.

The crude hydrocarbon mixture employed in the present invention preferably contains more than 5 weight percent of the tertiary olefin which contains one or more additional ethylenically or acetylenically unsaturated bonds, more preferably from about 6 to about 40 weight percent, and most preferably from about 10 to about 30 weight percent.

According to a preferred embodiment, the process of the present invention converts a crude hydrocarbon mixture which contains high charges of a tertiary olefin which contains one or more additional ethylenically or acetylenically unsaturated bonds, preferably isoprene, by the simultaneous etherification and hydrogenation. It is very surprising that at those high charges of isoprene the catalyst does not deactivate, whereas a product mixture is obtained which has an increased value because of its increased amount of alkyl tertiary alkyl ethers.

Preferably, the crude hydrocarbon mixture is a crude $C_4$- or $C_5$-hydrocarbon mixture, and especially a crude $C_5$-hydrocarbon mixture which contains one or both of 2-methyl-1-butene and 2-methyl-2-butene as tertiary olefin and isoprene as a gum-forming constituent.

The alcohols to be used in the present process are preferably saturated alkanols, for example primary alkanols having from 1 to 10 carbon atoms, more preferably 1 to 4 carbon atoms, and most preferably 1 to 2 carbon atoms. The most preferred alcohols are methanol and ethanol.

In the present process the molar ratio between the alcohol and etherifiable compounds present in the crude hydrocarbon mixture is preferably from 1 to 10. With the term etherifiable compounds is meant the tertiary olefins and the gum-forming constituents which are capable to react under the prevalent conditions with the alcohol to give desired ether compounds. Typically, branched multiple unsaturated compounds and especially those which contain a tertiary carbon atom which is also involved in a carbon-carbon double bond, such as for example isoprene, readily react with an alcohol to form an ether compound. A person skilled in the art can easily determine the amount of etherifiable compounds present in the starting crude hydrocarbon mixture, for example, by doing some introductory experiments. More preferably the molar ratio between the alcohol and the etherifiable compounds in the crude hydrocarbon mixture is from 1 to 4.

In the process of the present invention hydrogen is employed preferably in amount of from 1 to 10 moles of hydrogen per mole of carbon-carbon double bonds present in the gum-forming constituents, in excess of 1. In the present process, hydrogen is added to prevent the gum-forming constituents to form oligomers. Oligomerization can be avoided by selectively reacting away an excess of olefinic bonds to give a mono-olefin, or less desirable a saturated hydrocarbon, or by selectively hydrogenating excess carbon-carbon triple bond, in such a way as to form a mono-olefin or less desirable a saturated hydrocarbon. It is in general not desired to react away mono-olefinic bonds to give saturated compounds in the crude hydrocarbon mixture, as under those conditions less tertiary olefin will be available for etherification to the valuable alkyl tertiary alkyl ether. Therefore, the amount of hydrogen added should be adjusted with respect to the hydrogenation of the number of undesired, gum-forming carbon-carbon double or triple bonds in the gum-forming constituents. More preferably, hydrogen is used in amount of from 1 to 2 moles of hydrogen per mole of carbon-carbon double bonds present in the gum-forming constituents, in excess of 1. Hydrogen can be used in either pure form or in admixture with other gases. Typically, hydrogen is available in petrochemical industries in an impure form mixed with methane. Such impure hydrogen gases are suitable for use in the present process.

The temperature at which the present process is conducted preferably is from about 80° C. to about 140° C., and more preferably from about 100° C. to about 135° C. These temperature ranges are selected so as to avoid side reactions, for example dehydration of the alcohol reactant.

The crude hydrocarbon mixture can be used in the process of the present invention in the gaseous form or in the liquid form, but is preferably used in the liquid form.

The pressure is not critical and depends on whether a gaseous phase or a liquid phase is desired, as well as on the temperature. Preferably the pressure is between 1 and 50 bar.

The catalyst useful in the practice of this invention is a catalyst comprising an acidic molecular sieve containing an active hydrogenation metal component.

Molecular sieves and their preparation methods are well known and are, for example, described in *MOLECULAR SIEVES*, Principles of Synthesis and Identification, R. Szostak, Van Nostrand Reinhold, New York, 1989. The molecular sieves referred to in the present invention are described herein. The catalyst used in the present process requires the molecular sieve to have acidic properties. If not inherently acidic, the molecular sieve can be rendered acidic according to known methods, such as described in MOLECULAR SIEVES, ibid., pp 26–28. Suitable examples of acidic molecular sieves include acidic zeolites, acidic aluminum phosphates, acidic silicon aluminum phosphates and acidic carbon molecular sieves.

Suitable examples of acidic zeolites include 10-ring and 12-ring zeolites. Examples of suitable 10-ring zeolites include ZSM-5, Ferrierite, and ZSM-11. Examples of suitable 12-ring zeolites include Faujasite, Mordenite, Offretite, Zeolite Beta, and ZSM-12. Preferably, the acidic zeolite is a 12-ring zeolite. More preferably, the acidic zeolite is acidic Zeolite Beta or acidic Mordenite.

The acidic zeolite can be prepared in a known manner from a zeolite typically containing cations of the alkali or alkaline earth metals, or alternatively ammonium ions, for example, by treatment with acid to exchange the metal cations or ammonium ions against protons.

In the present process, it has been found very advantageous to employ an acidic zeolite, more preferably an acidic Zeolite Beta or acidic Mordenite Zeolite, which is dealuminated to provide a silica/alumina ratio of at least 15 and preferably at least 30.

The dealumination of zeolites is a method known per se and involves, for example, subjecting the zeolite to an acid treatment, preferably a strong acid, or a heat-treatment in the presence of steam or in an inert gas.

The acidic zeolites used in the present invention preferably have, apart from so-called micropores of a pore size less than 10 Å, a fraction of transitional pores of a pore size between 10 Å and 1000 Å. This transitional or secondary pore size structure is beneficial and provides better diffusional characteristics to the catalyst. The reactants can more easily enter and travel through the zeolite structure and the reaction products can easier and quicker exit the zeolite structure. This provides better reaction kinetics and a longer lifetime of the zeolite.

The transitional or secondary porosity can be introduced by subjecting the zeolite to, for example, a treatment with acid or heat. Such treatment usually also has the effect to remove aluminum atoms from the zeolite structure to thereby increase the silica/alumina molar ratio. The method used to determine pore volumes, both micro- and secondary pore volume, are described by S. Lowell in Introduction to Powder Surface Area (John Wiley and Sons, 1979), or in manuals provided with the Digisorb-6 instrument made by the Quantachrome Corporation.

Preferred acidic dealuminated mordenites and mordenite-like zeolites to be used as acidic molecular sieve in the present invention, as well as advantageous preparation processes therefor, are described in U. S. Pat. No. 4,891,448, which is incorporated herein by reference. The processes for converting the mordenite to the acidic form and for dealumination of the mordenites described in U. S. Pat. No. 4,891,448 can advantageously be applied on other zeolites as well.

The acidic molecular sieve can be used as such to prepare the catalyst to be employed in the present invention, or it can be made into an extrudate by compressing the acidic molecular sieve aggregates into binderless particles of suitable sizes. Alternatively, the acidic molecular sieve can be mixed with or made into an extrudate via use of binders well-known to those in the art. Suitable examples of binders include silicas, aluminas, clays and other oxide binders. Typically, the concentration of binder ranges from about 0 to about 90 weight percent of the bound acidic molecular sieve composition, preferably, from about 5 to about 70 weight percent, more preferably from about 5 to about 40 weight percent.

The catalyst to be employed in the present process comprises an acidic molecular sieve containing an active hydrogenation metal component. In general, any metal component having hydrogenation activity can be used. Exemplary of suitable hydrogenation metal components include one or more metals of groups 6, 7, 8, 9 and 10 of the Periodic Table of the Elements. Specific examples are: chromium, molybdenum, tungsten, manganese, rhenium, iron, cobalt, nickel, ruthenium, rhodium, palladium, osmium, iridium and platinum. A preferred active hydrogenation metal component comprises one or more of palladium, platinum and nickel. The active hydrogenation metal component is usually the substantially reduced and, preferably, the elemental form of the transition metals mentioned.

The amount of active hydrogenation metal component loaded on the acidic zeolite is not critical and it is typically present on the acidic molecular sieve in an amount of 0.001 to 20 weight percent, more preferably in an amount of 0.1 to 15 weight percent, based on the weight of the molecular sieve. For precious metals such as palladium, rhodium and platinum generally lower loadings are required than for less precious metals such as nickel or cobalt.

The active hydrogenation metal component can be loaded onto the acidic zeolite by any suitable method. Suitable methods for introducing the hydrogenation metal component include decomposition of volatile metal compounds such as metal carbonyls, introduction during synthesis of the zeolite, ion-exchange in a solution of the hydrogenation metal ion, solid state ion-exchange, as well as impregnation techniques. A preferred method comprises impregnating the acidic molecular sieve with a solution of a thermally decomposable and/or reducible compound of a metal having hydrogenation activity. The impregnation can be done according to the so-called incipient wetness or excess-solution techniques. In the incipient-wetness technique only so much of the impregnating solution is added to only fill up the pores of the acidic molecular sieve, whereafter the solvent is removed by applying heat or decreased pressure. In the excess-solution technique the acidic molecular sieve is suspended in the impregnating solution, followed by removal of the solvent by applying heat or decreased pressure. The solution of the metal is preferably aqueous, alcoholic or aqueous/alcoholic. Especially salts of the hydrogenation metal can be suitably loaded onto the acidic molecular sieve in these ways, and preferably the halide and nitrate salts.

The hydrogenation metal component loaded on the acidic molecular sieve can be converted to its active form, i.e., usually the substantially reduced or elemental form of the metal, in a reduction step. This reduction step can take place prior to charging the catalyst to the reaction zone, or in situ by the hydrogen present in the reaction mixture or feed. Typical reduction conditions are temperatures of 50 to 300° C. in a hydrogen atmosphere.

The catalyst employed in the present process shows no substantial deactivation in the conversion of crude hydrocarbon mixtures and remains active for prolonged periods of use. It has surprisingly been found that the catalyst used in the present process does not rapidly deactivate in case the hydrogen flow is interrupted, i.e., if no hydrogenation takes place. This is of great importance in commercial processes, as short interruptions in reactant flows occur regularly.

In case the catalyst shows substantial deactivation after prolonged periods of use, it may be regenerated by burning off the carbonaceous deposits or gums adhered. This may be effected by passing an oxygen containing gas over the catalyst at a temperature of 300°–700° C., and preferably of 400°–600° C.

The process of the present invention can be carried out in batch, semi-continuous, continuous flow or catalytic distillation processes. For continuous flow processes the weight hourly space velocity (when a catalyst bed is used) may vary within wide ranges, but is preferably from 0.1 to 10.

The following examples illustrate the invention without limiting it.

EXAMPLES 1 to 6

Preparation of the catalyst

The characteristics of the following acidic zeolites: Zeolite Beta, Zeolite Y, Zeolite ZSM-5, Mordenite Zeolite I, Mordenite Zeolite II and Mordenite Zeolite III; which are used to prepare the catalysts employed in the process of the present invention are given in Table 1. The acidic zeolites were prepared from the respective zeolites according to methods known per se.

Pellets of the acidic zeolites mentioned hereinbefore having a diameter of 1 to 3 mm are impregnated with a palladium solution according to the excess-solution technique, by suspending about 50 g of the respective acidic zeolite in about 200 ml of an aqueous solution of about 5.0 g/l of palladium$^{2+}$ tetraamine chloride. The suspension is stirred for two hours at room temperature, filtered, and the pellets rinsed with distilled water. The palladium-loaded acidic zeolite is then dried in air at 100° C., calcined during 16 hours at 600° C., and subsequently heated at 100° C. under hydrogen pressure during 16 hours to reduce the palladium salt. The amount of palladium on the catalyst which varies between 0.4 and 0.7 weight percent, calculated as palladium metal based on the weight of the respective acidic zeolite, is given in Table 1.

TABLE 1

| | CATALYST COMPOSITIONS | | | | | |
|---|---|---|---|---|---|---|
| Example No. | 1 | 2 | 3 | 4 | 5 | 6 |
| acidic zeolite | Y | beta | ZSM-5 | mordenite I | mordenite II | mordenite III |
| silica/alumina molar ratio | 80 | 30 | 150 | 81 | 123 | 220 |
| Surface area [m$^2$/g] | 750 | 700 | 400 | 355 | 388 | 386 |
| wt. % Pd | 0.7 | 0.7 | 0.6 | 0.4 | 0.6 | 0.7 |

Etherification/hydrogenation experiments

About 30 g of catalyst prepared according to the procedures described above is introduced into a continuous upflow reactor having a length of 0.88 m and an inner diameter of 2.1 cm which is heated by an electrical oven. 78.5 weight parts of a crude C$_5$-hydrocarbon mixture obtained from a light hydrocarbons steam cracker is conveniently mixed with 21.5 weight parts of methanol to provide a feed to the reactor having the composition as given in Table 3. In the same Table the composition of the reactor effluent is given as obtained in example 5 of the present invention. The total amount of gum-forming constituents in the feed to the reactor is 43.1 weight percent. The combined methanol and crude C$_5$-hydrocarbon mixture is pumped by a HPLC pump to the reactor. Hydrogen is supplied to the feed via a mass flow controller. The pressure is maintained at 22 bar to provide a liquid feed to the reactor. The weight hourly space velocity is maintained at about 0.5. All experiments are performed for 250 hours and the reactor effluent analyzed by gas chromatography. The relevant process conditions are specified in Table 2.

TABLE 2

HYDROCARBON CONVERSION PROCESS CONDITIONS

| Example No. | 1 | 2 | 3 | 4 | 5 | 6 |
|---|---|---|---|---|---|---|
| T [°C.] | 124 | 129 | 134 | 110 | 135 | 131 |
| $H_2$/dienes[a] [mole/mole] | 1.3 | 1.2 | 1.2 | 1.2 | 1.1 | 1.4 |
| Methanol/EC[b] molar ratio [mole/mole] | 2.2 | 2.2 | 2.2 | 2.2 | 2.2 | 2.2 |

[a]$H_2$/dienes is expressed as moles $H_2$ per mole isoprene and other dienes present in the feed to the reactor
[b]Methanol/EC molar ratio is expressed as moles of methanol per mole of etherifiable compounds (2-methyl-2-butene + 2-methyl-1-butene + isoprene)

TABLE 3

COMPOSITION OF REACTOR FEED AND EFFLUENT
(IN WEIGHT PERCENT)

| Compound | Feed | Effluent[a] |
|---|---|---|
| dimethylether | — | 1.0 |
| methanol | 21.5 | 17.5 |
| isopentane | 3.8 | 4.3 |
| 3-methyl-1-butene | 0.2 | 0.3 |
| 2-methyl-2-butene | 2.1 | 12.5 |
| 2-methyl-1-butene | 3.5 | 2.4 |
| isoprene | 15.3 | 0.06 |
| dienes | 27.8 | 0.8 |
| pentenes | 8.2 | 31.2 |
| saturated compounds | 12.8 | 13.8 |
| TAME | — | 8.3 |
| other compounds | 4.8 | 7.8 |

[a]The composition of the reactor effluent is for example 5.

Conversion of isoprene:

$$\frac{\text{(moles of isoprene in feed)} - \text{(moles of isoprene in effluent)}}{\text{(moles of isoprene in feed)}} \times 100\%$$

Etherifyable compounds (EC) conversion:

$$\frac{\text{moles of (2-methyl-1-butene + 2-methyl-2-butene + isoprene) converted}}{\text{moles of (2-methyl-1-butene + 2-methyl-2-butene + isoprene) in feed}} \times 100\%$$

Conversion of Dienes:

$$\frac{[(\text{wt \% dienes (excluding isoprene) in feed})] - [(\text{wt \% dienes (excluding isoprene) in effluent}]}{\text{wt \% dienes (excluding isoprene) in feed}} \times 100\%$$

Selectivity to TAME:

$$\frac{\text{moles of TAME produced}}{\text{moles of (isoprene + 2-methyl-1-butene + 2-methyl-2-butene) converted}} \times 100\%$$

Yield to TAME: Selectivity to TAME × EC conversion

Selectivity to isopentane:

$$\frac{\text{(moles of isopentane produced)}}{\text{moles of (isoprene + 2-methyl-1-butene + 2-methyl-2-butene) converted}} \times 100\%$$

Selectivity to 3-methyl-1-butene:

$$\frac{\text{moles of 3-methyl-1-butene produced}}{\text{moles of (isoprene + 2-methyl-1-butene + 2-methyl-2-butene) converted}} \times 100\%$$

TABLE 4

RESULTS (EXPRESSED IN PERCENTAGES)

| Example No. | 1 | 2 | 3 | 4 | 5 | 6 |
|---|---|---|---|---|---|---|
| conversion of isoprene | 99.8 | 100 | 99.9 | 98.2 | 99.6 | 99.7 |
| EC conversion | 15.4 | 38.7 | 27.8 | 46.2 | 31.4 | 27.8 |
| conversion of Dienes | 97.5 | 98.2 | 98.0 | 95.6 | 97.1 | 97.6 |
| selectivity to TAME | 74.6 | 91.2 | 84.4 | 81.5 | 91.1 | 89.3 |
| yield to TAME | 11.5 | 35.3 | 23.5 | 37.7 | 28.6 | 24.8 |
| selectivity to isopentane | 16.6 | 8.1 | 11.0 | 6.0 | 6.7 | 9.4 |
| selectivity to 3-methyl-1-butene | 8.8 | 0.7 | 4.6 | 12.5 | 2.2 | 1.9 |

EXAMPLE 7

About 30 g of the catalyst used in Example 5 is introduced into the continuous upflow reactor described in Examples 1–6. 70 Weight parts of a crude C4-hydrocarbon mixture obtained from a light hydrocarbon steam cracker is conveniently mixed with 30 weight parts of methanol to provide a feed to the reactor having the composition as given in Table 5. The total amount of gum-forming constituents is 23.2 weight percent. Hydrogen is supplied to the feed via a mass flow controller. The pressure is maintained at 22 bar to provide a liquid feed to the reactor. The experiment is performed for 250 hours and the reactor effluent analyzed by gas chromatography. The relevant process conditions are specified in Table 6. The composition of the reactor effluent is given in Table 5.

TABLE 5

COMPOSITIONS OF REACTOR FEED AND EFFLUENT
(IN WEIGHT PERCENT)

| | Feed wt % | Reactor outlet wt % |
|---|---|---|
| methanol | 30.0 | 18.6 |
| isobutane | 0.8 | 1.0 |
| n-butane | 3.6 | 4.4 |
| trans-butene-2 | 4.8 | 14.5 |
| butene-1 | 12.4 | 22.1 |
| isobutylene | 23.0 | 2.3 |
| cis-butene-2 | 2.2 | 4.0 |
| butadiene-1,3 | 23.2 | 1.6 |
| MTBE | — | 31.0 |
| other ethers | — | 0.5 |

TABLE 6

PROCESS CONDITIONS

| | |
|---|---|
| T [°C.] | 100 |
| $H_2$/dienes[a] [mole/mole] | 1.3 |
| Methanol/EC[b] molar ratio [mole/mole] | 2.3 |
| Weight hourly space velocity | 0.5 |

[a]$H_2$/dienes is expressed as moles $H_2$ per mole butadiene present in the feed
[b]Methanol/EC molar ratio is expressed as moles of methanol per mole of isobutylene The conversion of isobutylene in this example is 90%, and the conversion of 1,3-butadiene is 93%. The selectivity to MTBE is 97%.

What is claimed is:

1. A process for conversion of crude hydrocarbon mixtures comprising tertiary olefins and gum-forming constituents, which process comprises contacting the crude hydrocarbon mixture with an alcohol and hydrogen in the presence of a catalyst comprising an acidic mordenite zeolite containing an active hydrogenation metal component.

2. Process according to claim 1 wherein the crude hydrocarbon mixture contains more than 5 weight percent of the gum-forming constituents.

3. Process according to claim 2 wherein the crude hydrocarbon mixture contains about 6 to about 70 weight percent of the gum-forming constituents.

4. Process according to claim 1 wherein the crude hydrocarbon mixture comprises at least one tertiary olefin selected from the group consisting of isobutylene, 2-methyl-1-butene, 2-methyl-2-butene, 2-methyl-1-pentene, and 2-methyl-2-pentene.

5. Process according to claim 1 wherein the gum-forming constituent comprises a tertiary olefin which contains one or more additional ethylenically or acetylenically unsaturated bonds.

6. Process according to claim 5 wherein the crude hydrocarbon mixture contains more than 5 weight percent of the tertiary olefin which contains one or more additional ethylenically or acetylenically unsaturated bonds.

7. Process according to claim 6 wherein the crude hydrocarbon mixture contains about 6 to about 40 weight percent of the tertiary olefin which contains one or more additional ethylenically or acetylenically unsaturated bonds.

8. Process according to claim 5 wherein the tertiary olefin which contains one or more additional ethylenically or acetylenically unsaturated bonds comprises isoprene.

9. Process according to claim 1 wherein the crude hydrocarbon mixture is a crude $C_5$-hydrocarbon mixture containing one or both of 2-methyl-1-butene and 2-methyl-2-butene as tertiary olefin and isoprene as gum-forming constituent.

10. Process according to claim 1 wherein the alcohol is a primary alkanol having from 1 to 10 carbon atoms.

11. Process according to claim 1 wherein the crude hydrocarbon mixture contains etherifiable compounds and wherein the molar ratio between the alcohol and etherifiable compounds present in the crude hydrocarbon mixture is from 1 to 10.

12. Process according to claim 11 wherein the molar ratio between the alcohol and etherifiable compounds is from 1 to 4.

13. Process according to claim 1 wherein hydrogen is employed in an amount of from 1 to 10 moles of hydrogen per mole of carbon-carbon double bonds present in the gum-forming constituents, in excess of 1.

14. Process according to claim 13 wherein hydrogen is employed in an amount of from 1 to 2 moles of hydrogen per mole of carbon-carbon double bonds present in the gum-forming constituents, in excess of 1.

15. Process according to claim 1 wherein the process is conducted at a temperature from about 80° C. to about 140° C.

16. Process according to claim 15 wherein the temperature is from about 100° C. to about 135° C.

17. Process according to claim 1 wherein the acidic mordenite zeolite is a dealuminated mordenite zeolite having a silica/alumina molar ratio of at least 15.

18. Process according to claim 1 wherein the active hydrogenation metal component comprises one or more metals of groups 6, 7, 8, 9 or 10 of the Periodic Table of the Elements.

19. Process according to claim 18 wherein the active hydrogenation metal component comprises one or more of palladium, platinum and nickel.

20. Process according to claim 1 wherein the active hydrogenation metal component is present on the mordenite zeolite in an amount of from 0.001 to 20 weight percent, based on the weight of the molecular sieve.

21. Process according to claim 20 wherein the active hydrogenation metal component is present on the mordenite zeolite in an amount of from 0.1 to 15 weight percent, based on the weight of the molecular sieve.

22. A process for conversion of a tertiary olefin which contains one or more additional ethylenically or acetylenically unsaturated bonds, which process comprises contacting the hydrocarbon compound, an alcohol, and hydrogen with a catalyst comprising an acidic mordenite zeolite containing an active hydrogenation metal component.

* * * * *